United States Patent

Chasanoff et al.

[11] 4,050,156
[45] Sept. 27, 1977

[54] DENTAL APPLIANCE

[76] Inventors: Daniel Chasanoff, 33 Ardslay Drive;
Myles Z. Schneider, 18 Windgate
Drive, both of New City, N.Y. 10956

[21] Appl. No.: 700,198

[22] Filed: June 28, 1976

[51] Int. Cl.² ............................................. A61C 13/00
[52] U.S. Cl. ................................................ 32/2; 32/8;
32/14 A
[58] Field of Search .............................. 32/14 A, 2, 8

[56] References Cited
U.S. PATENT DOCUMENTS 3,303,565  2/1967  Newman ........................... 32/14 A
3,504,438  4/1970  Wittman et al. ..................... 32/14 A Primary Examiner—Robert Peshock
Attorney, Agent, or Firm—Stanley J. Yavner

[57] ABSTRACT

Dental appliances such as orthodontic apparatus in the form of a coated metal having characteristics including aesthetic appearance highlighted by tooth coloring, resistance to abrasion, low friction, weldability, stability at high temperatures and attachability to dental adhesives. A base metallic material is covered by a coating including a para-oxybenzoyl homopolyester and polytetrafluoroethylene and a pigment for providing the tooth coloring.

6 Claims, 5 Drawing Figures

DENTAL APPLIANCE

This invention relates primarily to dental appliances and more particularly to dental appliances for securement within the oral cavity to present a compatible aesthetic appearance in connection with teeth.

For years now, the fields of dentistry and orthodontics have been presented with a multi-faceted problem with respect to providing dental appliances such as crowns, bands, brackets, wires, etc. for use in the oral cavity without incompatible appearance characteristics. For instance, for years orthodontic appliances have been provided in various metals and there is no question that such metal materials are the best possible materials in terms of strength, securement, capability and abrasion resistance. However, it is also well known that such metal materials are totally incompatible with teeth in terms of appearance. This is particularly important when it is noted that orthodontic appliances are used for teenagers whose psychological balance and well-being are of prime concern. Peer pressure is a sensitivity that must be dealt with in young adults and appearance is usually one of the objects of such pressure.

Thus, those skilled in this art have attempted to create various alternatives to the metal dental appliances. Crowns, orthodontic appliances and other apparatus have been manufactured totally of plastic materials as a substitute for the metal materials previously used. Plastic materials, however, have suffered from various drawbacks; namely, a lack of abrasion resistance, lack of strength, brittleness and propensity to staining which are but a few examples. Also, coatings have been attempted, for instance with acrylics, porcelains and pure Teflon (polytetrafluoroethylene). Such coatings suffer from similar drawbacks, especially with respect to securing such coated appliances with an adhesive. It has been found that the adhesive attacks the coating and/or the adhesive does not attach to the coating and/or the coating may be easily abraded. It should also be pointed out that, for instance, various pure Teflon coated appliances have required either spaces in the coating or removability of portions of the coating in order to attach such appliances by use of an adhesive or welding.

Accordingly, a primary object of the present invention is to provide dental appliances offering a pleasing aesthetic appearance.

A further object of the present invention is to provide dental appliances with the above characteristic and having high resistance to abrasion, compatibility with dental adhesives, ability to be secured by welding, low-friction characteristics and presenting a tooth colored appearance.

A still further object of the present invention is to provide a dental appliance possessing strength characteristics, toughness, chemical inertness and resistance to heat, bacteria and acid attack.

These and other objects of the present invention are provided in a dental appliance which features a metallic base material and a coating including a para-oxybenzoyl homopolyester, polytetrafluoroethylene and a pigment for providing a tooth colored appearance. The coating materials include proportions by volume of 20–55% para-oxybenzoyl homopolyester and 80–45% polytetrafluoroethylene, preferably 45% para-oxybenzoyl homopolyester and 55% polytetrafluoroethylene. One typical pigment useful in providing the tooth coloring for the coating is $TiO_2$.

The above brief description, as well as further objects, features and advantages of the present invention will be more fully appreciated by reference to the following detailed description of the preferred, but nonetheless illustrative, embodiment, when taken in conjunction with the accompanying drawings, wherein.

Figure 1:
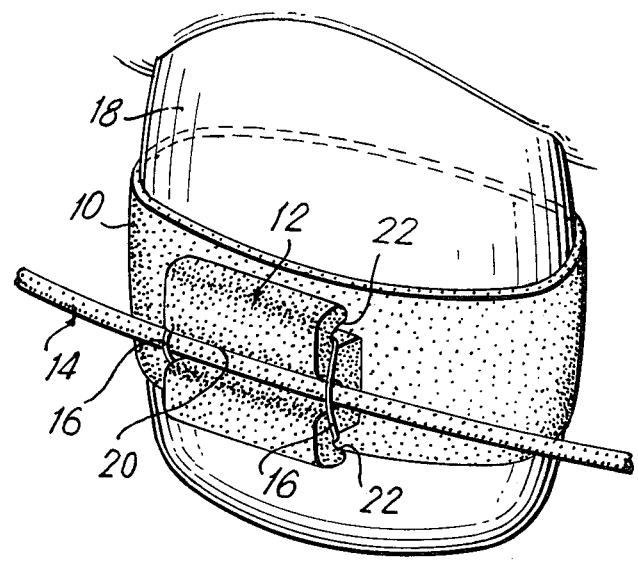
FIG. 1 is a pictorial representation of an orthodontic appliance prepared in accordance with the present invention, in situ.

With reference to the drawings, and particularly FIG. 1 thereof, an orthodontic apparatus assembly is shown, by way of example, to include a band 10, a bracket 12, an arch wire 14 and ligature wires 16. Specifically, band 10 is formed of a metal base material and encircles tooth 18. Of course, in a complete orthodontic assembly, a plurality of teeth 18 will be involved and a number of bands 10 will be used according to the extent of orthodontic repair necessary. Bracket 12 is illustrated in FIG. 1 to be an edgewise bracket which is typically for the purposes of guiding the rehabilitation motion of arch wire 14. For this purpose, its primary feature is a horizontally disposed slot 20 slightly oversized with respect to arch wire 14 so that horizontal motion of arch wire 14 is permitted. For its ligating function, edgewise bracket 12 includes a pair of slots 22 defined generally rearwardly of the bracket. Ligature wires 16 are disposed in slots 22 and wrap forwardly of arch wire 14 in order to retain arch wire 14 with respect to forward motion within slot 20. As with band 10, bracket 12 is of a metal base material and is welded or otherwise affixed to band 10.

Of course, band 10 is cemented (dental cement) or otherwise attached to tooth 18.

As described in the foregoing, the orthodontic assembly is representative of the prior art metal assemblies. Such assemblies are strong, durable, useable with attachment techniques involving cement and/or welding, as well as others, and generally totally satisfactory except for aesthetic appearance.

In terms of aesthetic appearance, the orthodontic assembly as thus described has two basic drawbacks: firstly, the aesthetic appearance is marred by the startingly vivid contrast between the metal assembly and the white tooth background; secondly, the aesthetic appearance is marred by the common occurrence with respect to food particles being trapped at various points of the assembly. As to the latter point, food particles are easily trapped by the metal components providing breeding areas for bacterial growth leading to tooth decay.

The present invention offers an advantage over the metal appliances and also over plastic appliances and plastic coated metal appliances now common in the art. Such advantages are enabled by the orthodontic structures of the present invention including a metal base with a coating (represented by the stippling of FIG. 1 and other figures of the drawing) comprising para-oxybenzoyl homopolyester and a polymeric fluorocarbon and co-polymers and including a pigment for providing a tooth colored appearance. Such a coating offers its advantages because of its resistance to abrasion, its ability to be welded, its low-friction characteristic, its ability to withstand attack by either acid or food, its compatibility with dental adhesives and cements and its stability at high temperatures.

Figure 2:
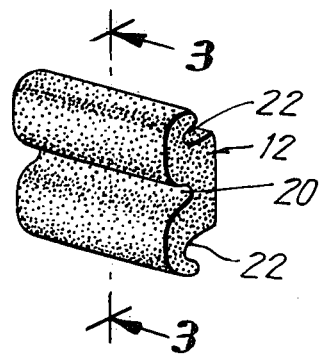
FIG. 2 is an isometric illustration of the orthodontic appliance shown in FIG. 1 as prepared in accordance with the present invention.

FIG. 2 illustrates the bracket 12 of the orthodontic assembly of FIG. 1 and shows the capability of the present invention with respect to coating metal base parts thereof individually prior to assembly.

Figure 3:
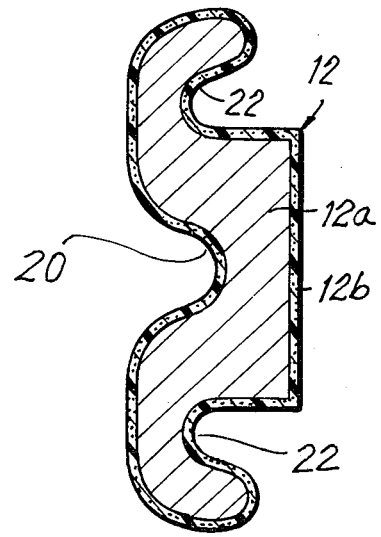
FIG. 3 is a cross-sectional representation of the appliance of FIG. 2 taken along the line 3—3 of FIG. 2 and showing particularly the structure thereof.

FIG. 3 is a cross-sectional view of the bracket of FIG. 2 and indicates the metal base material 12a coated with Teflon (a polymeric fluorocarbon such as polytetrafluoroethylene) and Ekonol (para-oxybenzoyl homopolyester), as examples. Also included in coating 12b is a pigment such as $TiO_2$ to provide a tooth colored appearance for the parts of the orthodontic assembly.

Figure 4:
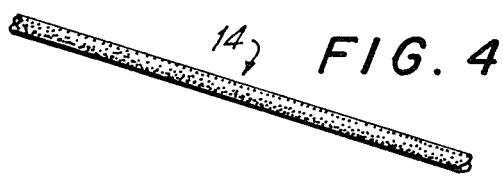
FIG. 4 is an isometric representation of the present invention used in connection with an orthodontic arch wire.
Figure 5:
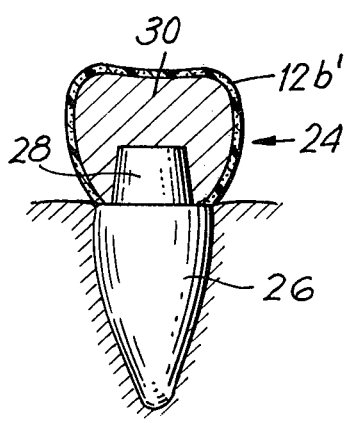
FIG. 5 is an isometric representation of the present invention as used in connection with a tooth crown.

Of course, FIGS. 4 and 5 illustrate a coated arch wire 14 and a coated crown 24, provided according to the present invention. The crown 24 of FIG. 5 is particularly shown to illustrate the usefulness of the present invention with other than orthodontic assembly parts. FIG. 5 shows a base tooth structure 26 upwardly extending from which is protrusion 28 for receiving crown 24. Crown 24 itself is similarly structured with a metal base material 30 covered with coating 12b'.

It is known that Ekonol and other para-oxybenzoyl homopolyesters can be applied in coatings with commercially available equipment. However, the characteristics are immeasurably improved by the use of Teflon material and a pigment in a coating for metal dental appliances.

The coating, according to the present invention is provided by preparing a water dispersion of particles wherein the Teflon forms a sub-microscopic fibrous matrix within the Ekonol and the resulting material is provided as a coating by either spreying or applying the coating in powder form. The desired characteristics of the coated metal base dental appliance is best achieved by the use of a pigment usch as $TiO_2$ for the purposes of tooth coloring to make the appliance more compatible for its intended use. Heat, at a temperature of more than 600° F, is used in preparing the coating.

Proportions of the materials making up the coatings may be in the range of (by volume) 20% to 55% para-oxybenzoyl homopolyester (Ekonol) and 80% to 45% polytetrafluoroethylene. Of course, all percentages are in terms of proportion by volume.

What is claimed is:

1. A dental appliance, for use in the mouth as an improvement over polymeric fluorocarbon appliances, comprising a metallic base material and a coating including a para-oxybenzoyl homopolyester, a polymeric fluorocarbon and a pigment for providing a tooth colored appearance.

2. The invention according to claim 1 wherein said appliance is an orthodontic appliance and said coating is attachable to an adhesive without attack therefrom.

3. The invention according to claim 1 wherein said polymeric fluorocarbon is polytetrafluoroethylene.

4. The invention according to claim 3 wherein said coating including said materials in proportions by volume of 20% - 55% para-oxybenzoyl homopolyester and 80% - 45% polytetrafluoroethylene.

5. The invention according to claim 3 wherein said coating includes said materials in proportions by volume of 45% para-oxybenzoyl homopolyester and 55% polytetrafluoroethylene.

6. The invention according to claim 3 wherein said pigment to $TiO_2$.

* * * * *